(12) United States Patent
Wahlgren et al.

(10) Patent No.: US 7,970,478 B2
(45) Date of Patent: Jun. 28, 2011

(54) OPTIMIZING STIMULATION THERAPY OF AN EXTERNAL STIMULATING DEVICE BASED ON FIRING OF ACTION POTENTIAL IN TARGET NERVE

(75) Inventors: Stephen Wahlgren, Easton, PA (US); Michael R. Tracey, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 197 days.

(21) Appl. No.: 12/317,194

(22) Filed: Dec. 19, 2008

(65) Prior Publication Data

US 2010/0161005 A1    Jun. 24, 2010

(51) Int. Cl.
*A61N 1/00* (2006.01)
(52) U.S. Cl. .......................................... 607/62
(58) Field of Classification Search .................. 600/300, 600/372, 544; 607/2, 46, 57, 61, 62, 48, 607/544
See application file for complete search history.

(56) References Cited

U.S. PATENT DOCUMENTS

| 6,473,652 | B1 | 10/2002 | Sarwal et al. | |
|---|---|---|---|---|
| 2005/0153885 | A1* | 7/2005 | Yun et al. | 514/12 |
| 2005/0277998 | A1 | 12/2005 | Tracey et al. | |
| 2006/0195153 | A1 | 8/2006 | DiUbaldi et al. | |
| 2009/0157147 | A1* | 6/2009 | Cauller et al. | 607/61 |

OTHER PUBLICATIONS

International Search Report and Written Opinion dated Mar. 2, 2010 for counterpart International PCT Application No. PCT/US2009/065327 (13 pages).
Tomek et al., "Gastric Motility and Volume Sensing by Implanted Magnetic Sensors," Sensor Letters, vol. 5, No. 1 (2007) pp. 276-278.

* cited by examiner

*Primary Examiner* — George Manuel
*Assistant Examiner* — Robert N Wieland
(74) *Attorney, Agent, or Firm* — Cheryl F. Cohen

(57) ABSTRACT

A method and system for optimizing stimulation therapy of an external stimulating device. The stimulating signal for stimulation of a target nerve is produced using the external stimulating device. A magnetic field is induced in an implanted transmitting coil disposed proximate the target nerve when the action potential is fired along an axon of the target nerve. In turn, a feedback signal is generated in a receiving coil associated with the external stimulating device based on whether the target nerve fires an action potential. Stimulating signal parameters of the stimulating signal are adjusted based on the feedback signal.

18 Claims, 2 Drawing Sheets

200 Generating a stimulating signal for stimulation of a target nerve using an external stimulating device 205 Producing a feedback signal based on whether the target nerve fires an action potential 210 Adjusting a stimulating signal parameter of the stimulating signal based on the feedback signal

OPTIMIZING STIMULATION THERAPY OF AN EXTERNAL STIMULATING DEVICE BASED ON FIRING OF ACTION POTENTIAL IN TARGET NERVE

BACKGROUND OF THE INVENTION

1. Field of the Invention

The present invention is directed to a system and method for detecting or monitoring of action potential firing in a target nerve and based on such feedback information optimizing stimulating therapy for an external nerve stimulating device.

2. Description of Related Art

External electrical stimulating devices are well known and used for stimulating nerves such as the pudendal nerve, sacral nerve, median nerve, ulnar nerve, transpalmar median nerve, or any other nerve. Nerve stimulation is a process by which a specific target nerve is stimulated using external electrodes that generate electrical pulses having a particular frequency, amplitude and waveform. A nerve cell can be excited by increasing the electrical charge within the nerve, thus increasing the membrane potential inside the nerve with respect to the surrounding extracellular fluid. An action potential (AP) occurs when a neuron sends information down an axon or fiber. The action potential is an electrical impulse or spike that is created by a depolarizing current and propagates down the length of the axon. Electrical stimulation from an external stimulation device can trigger the firing of an action potential.

A threshold stimulus intensity is defined as that required to trigger an action potential. The action potential is an all or nothing principle. That is, the action potential will only be fired by the neuron and the signal propagated along the axon if the neuron reaches this threshold stimulus intensity. The amplitude of an action potential for a particular nerve is substantially constant and independent of the amount of stimulus current. So long as the threshold stimulus intensity is reached, the neuron will fire an action potential having a substantially constant or fixed amplitude. Instead, the frequency of the action potential is what determines the intensity of the stimulus. The information in the nervous system is therefore coded by frequency of firing rather than the amplitude of the action potential.

External nerve stimulating devices or stimulators are advantageous due to their relatively inexpensive cost of manufacture in comparison to implantable stimulating devices and noninvasive ability to stimulate a nerve without requiring surgery or implantation. However, because the stimulating device is external to the body, there exists the possibility of improper alignment or positioning of the stimulating device thereby undesirably stimulating a non-target nerve without stimulation of the target nerve. If the electrical stimulating current is too large, it is possible to undesirably stimulate non-target nerves simultaneously with the target nerve. In addition, the amplitude of the stimulation current if too large may cause undesirable physical discomfort, temporary or even permanent tissue damage to surrounding tissue, or expend too much energy from a power source limited due to its relatively small size. On the other hand, if the amplitude of the stimulation current is too small the stimulator may not be effective in stimulating the target nerve.

It is therefore desirable to develop an improved method and system for optimizing stimulation therapy by monitoring firing of an action potential and providing a feedback signal for adjusting of stimulating signal parameters.

SUMMARY OF THE INVENTION

The present invention is directed to an improved method and system for optimizing stimulation therapy by monitoring firing of an action potential and providing a feedback signal for adjusting of stimulating signal parameters.

Another aspect of the present invention is directed to a method and system for optimizing stimulation therapy of an external stimulating device. The stimulating signal for stimulation of a target nerve is produced using the external stimulating device. A magnetic field is induced in an implanted transmitting coil disposed proximate the target nerve when the action potential is fired along an axon of the target nerve. In turn, a feedback signal is generated in a receiving coil associated with the external stimulating device based on whether the target nerve fires an action potential. Stimulating signal parameters of the stimulating signal are adjusted based on the feedback signal.

Still another aspect of the present invention is directed to a system for optimizing stimulation therapy. The system includes a transmitting coil implantable proximate a target nerve, wherein the transmitting coil generates a magnetic field induced therein when an action potential fires along an axon of the target nerve. In addition, the system includes an external stimulating device for generating a stimulating signal for stimulation of the target nerve. The external stimulating device has a receiving coil for producing a feedback signal based on the generated magnetic field induced in the transmitting coil and a processor for adjusting a stimulating signal parameter of the stimulating signal based on the feedback signal.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
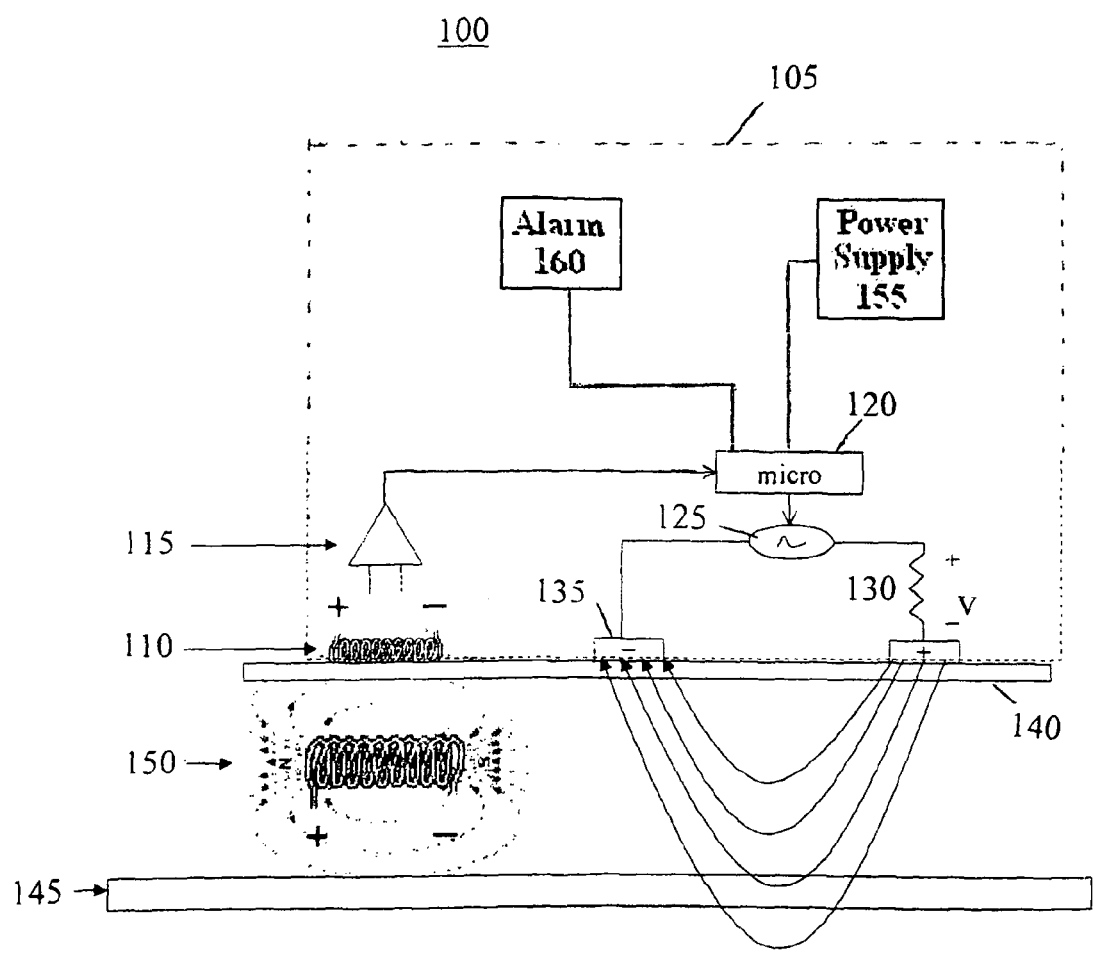
FIG. 1 is an exemplary system in accordance with the present invention for optimizing stimulation therapy for an external stimulating device based on monitoring of the firing of an action potential.

FIG. 1 is an exemplary system 100 in accordance with the present invention for optimizing stimulation therapy delivered by an external nerve stimulating device or stimulator 105 based on detection or monitoring of the firing of an action potential. Stimulating device 105 is external to the body and proximate to or in direct contact with the skin 140. U.S. Patent Publication 2005/0277998, assigned to the same entity as the present invention the disclosure of which is hereby incorporated by reference in its entirety, discloses an external transdermal patch stimulating device, however, other external stimulating devices are contemplated and within the intended scope of the present invention.

A pickup or receiving electrode 110 is associated with the external stimulating device 105 for generating a voltage from a received inductive field, to be described in detail below. In turn the voltage signal generated by the pickup or receiving electrode 110 is preferably processed by signal conditioning and amplification circuitry 115. The processed and amplified output signal is received as input to a microprocessor 120. Based on the inductive field received by the pickup or receiving electrode 110, microprocessor 120 adjusts, whenever appropriate, one or more stimulating signal parameters such as amplitude, frequency and even the waveform itself. Microprocessor 120 may be a digital signal processor, controller or processor. A waveform generator 125 generates a waveform based on the adjusted stimulating signal parameters received from the microprocessor 120. An inline resistive element 130 with a known resistance (relatively small resistance) is electrically connected to waveform generator 125. The voltage V of the resistive element 130 is directly proportional to the output current of the waveform generator 125 by the relationship established under Ohm's law (V=IR). Surface leads or electrodes 135 generate a stimulating signal that penetrates through the skin 140 to stimulate the target nerve of interest 145. Power source 155, typically a battery, provides energy to the external stimulating device 105.

Implantable or internal transmitting coil 150 is a relatively small implantable coil or inductor preferably wrapped about a core having a relatively high permeability (e.g., magnetic core). The transmitting coil 150 is positioned proximate a target nerve 145 to detect or monitor the firing of an action potential along the axon of the target nerve. As an action potential travels down the length of the axon an electric voltage is generated across the windings of the implantable transmitting coil 150. This voltage, in turn, induces in the implantable transmitting coil 150 a magnetic field or magnetic flux proportional to the voltage.

External pickup or receiving coil 110 detects the magnetic field generated by the implantable transmitting coil 150. Specifically, the magnetic field or magnetic flux generated by the implantable transmitting coil 150 passes through the windings in the external pickup or receiving coil 110 thereby generating a voltage across the coil. In a preferred embodiment, signal conditioning circuitry and an amplifier 115 are preferably included to remove any noise and amplify the signal. Microprocessor 120 in the external stimulating device 105 adjusts the stimulating signal parameters in accordance with the feedback signal induced in the external pickup coil 110.

In operation, the external stimulating device 105 is positioned in contact with or proximate the skin 140 in proximity to the implantable transmitting coil 150 and target nerve 145. When activated, the external stimulating device 105 produces an electrical stimulus signal directed at a target nerve 145. The stimulus signal is recognized as having reached the target nerve 145 if the action potential is fired for that nerve. Firing of the action potential generates an electrical pulse that, in turn, generates a voltage across the windings of the implantable transmitting coil 150 as the pulse propagates along the axon. A magnetic field or magnetic flux proportional to the voltage is induced in the implantable transmitting coil 150. External to the body, the pickup or receiving coil 110 detects the inductive field generated by the implantable transmitting coil 150. The detected inductive field, in turn, generates a voltage feedback signal across the pickup or receiving coil 110. Processing is preferably performed on the received feedback signal that increases its amplitude and removes unwanted noise. The processed feedback signal is received as input to microprocessor 120. In the present case, since the feedback signal is greater than zero indicating that the target nerve was stimulated and an action potential was fired, no adjustment will be made by the microprocessor 120 to the stimulating signal parameters.

If the stimulus signal generated by the external stimulating device 105 does not stimulate the target nerve 145 the target neuron will not reach the threshold stimulus intensity and as a result the graded depolarization will not generate an action potential. Accordingly, the signal or information will not be propagated along the axon. The failure to stimulate the target nerve may be due to any number of factors such as the intensity or amplitude of the stimulus signal, increased impedance of the skin or other factors. Under such circumstances, the internal or implantable transmitting coil 150 will not generate a voltage and thus not generate a magnetic field or magnetic flux. In the absence of any magnetic field or magnetic flux, external pickup coil 110 will not generate a voltage thereby alerting or signaling to the microprocessor 120 to adjust one or more stimulating signal parameters to increase the stimulating signal. In a preferred embodiment, microprocessor 120 will implement a predetermined stepwise adjustment that has been preprogrammed. By way of illustrative example, the predetermined stepwise adjustment will be 0.5 V increments, however, any stepwise increment may be set, as desired. This feedback loop continues to provide information until the occurrence of an action potential is detected. The stimulating signal parameters are maintained without adjustment so long as an action potential is detected.

If microprocessor 120 increases the stimulating signal to a predetermined maximum threshold allowed by the system without detecting the firing of an action potential in the target nerve 140, preferably an alarm 160 (e.g., audible, visual and/or tactile) is activated and/or the external stimulating device 105 is automatically shut off to prevent harm to the patient and conserve power. The predetermined maximum threshold may be reached without firing of an action potential for any number of reasons including, but not limited to: (i) inaccurate positioning of the external stimulating device relative to the internal coil; (ii) dirt, particulate or other impurities on the surface of the stimulating device; and/or (iii) increased skin impedance.

Figure 2:
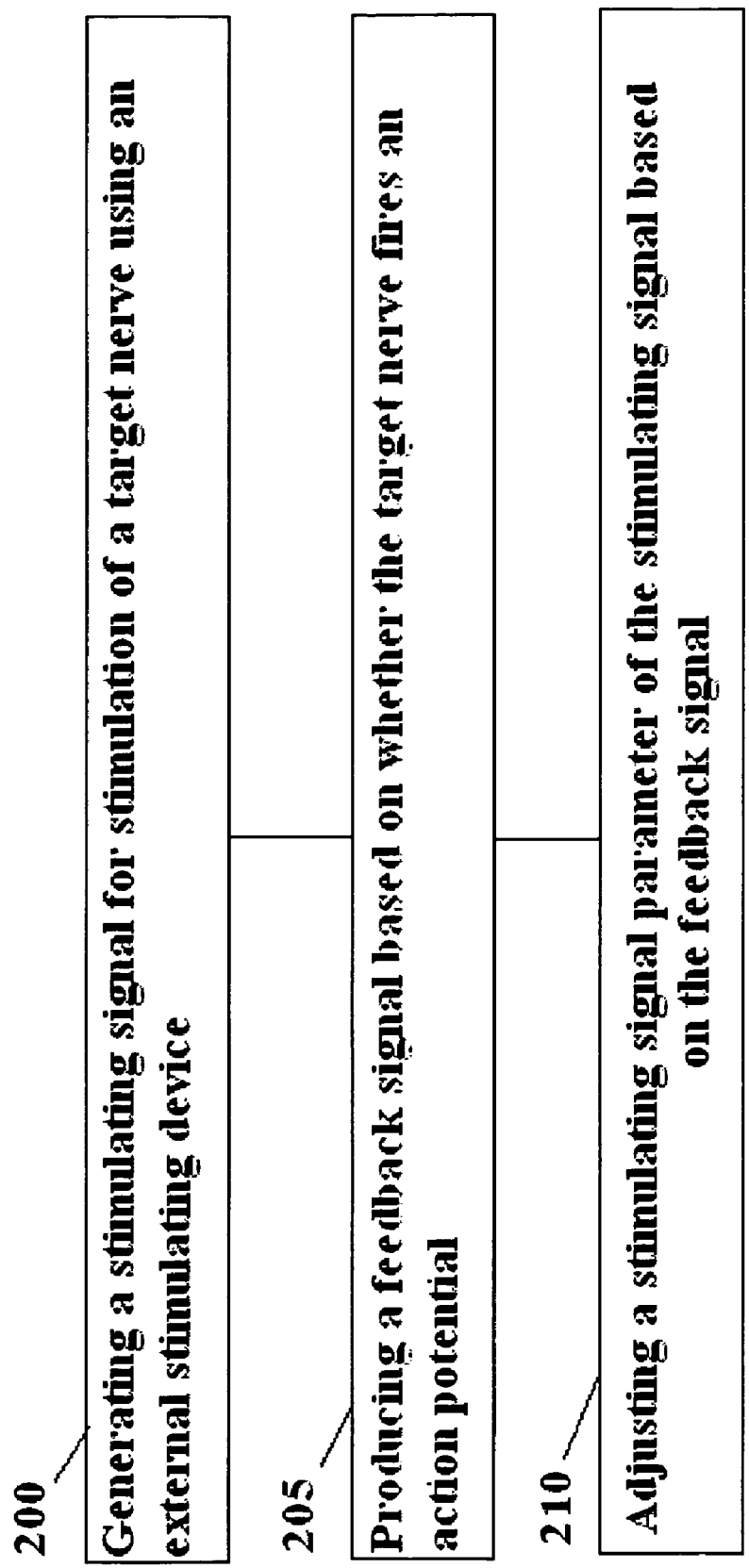
FIG. 2 is a flow chart of the functionality in accordance with the present inventive method of optimizing stimulation therapy for an external stimulating device.

FIG. 2 represents an exemplary flow chart of the high level functionality in accordance with the optimization of stimulation therapy method of the present invention. Initially, in step 200 a stimulating signal for a target nerve is generated by the external stimulating device. A feedback signal is produced by the implantable transmitting coil and received by the external stimulating device in step 205 based on whether an action potential has been fired at the target nerve. Stimulating signal parameters associated with the stimulating signal are adjusted by the external stimulating device based on the received feedback signal, in step 210.

The present inventive system and method for optimizing stimulation therapy is applicable to any external stimulating device irrespective of whether in the form or a transdermal patch or otherwise. Moreover, the present invention may be combined with other systems and methods for adjustment of stimulating signal parameters by the patient, physician or clinician as well as adjustments for skin impedance.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for optimizing stimulation therapy for an external stimulating device, comprising the steps of:
   generating a stimulating signal for stimulation of a target nerve using the external stimulating device;
   producing a feedback signal based on whether the target nerve fires an action potential; and
   adjusting a stimulating signal parameter of the stimulating signal based on the feedback signal;
   wherein the producing step comprises the step of generating a magnetic field induced in an implanted transmitting coil disposed proximate the target nerve when the action potential fires along an axon along the target nerve in response to the generated stimulating signal produced by the external stimulating device: grid the feedback signal is produced in a receiving coil associated with the external stimulating device based on the generated magnetic field induced in the implanted transmitting coil.

2. The method in accordance with claim 1, wherein the implanted transmitting coil serves a dual function of monitoring the firing of the action potential along the axon of the target nerve and inducing the feedback signal in the receiving coil of the external stimulating device.

3. The method in accordance with claim 1, wherein the producing step further comprises the step of processing and amplifying the feedback signal in the receiving coil using signal conditioning and amplification circuitry.

4. The method in accordance with claim 1, wherein the adjustment of the stimulating signal parameter is performed by a processor.

5. The method in accordance with claim 1, wherein the stimulating signal parameter is one of amplitude, frequency or a waveform itself.

6. The method in accordance with, claim 1, wherein the adjusting step comprises, when the feedback signal is zero, indicating that the target nerve was not stimulated nor was the action potential fired, adjusting the stimulating signal parameter; whereas when the feedback signal is greater than zero indicating that the target nerve was stimulated and the action potential was fired, no adjustment is made to the stimulating signal parameter.

7. The method in accordance with claim 1, wherein adjustment of the stimulating signal parameter is in predetermined increments.

8. The method in accordance with claim 7, wherein adjustment of the stimulating signal parameter is in increments of approximately 0.5 V.

9. The method in accordance with claim 6, wherein the adjusting step further comprises, at least one of activating an alarm and shutting off the external stimulating device, if the adjusted stimulating signal parameter exceeds a predetermined maximum threshold allowed without detecting the firing of the action potential in the target nerve.

10. A system for optimizing stimulation therapy, comprising:
    a transmitting coil implantable proximate a target nerve, the transmitting coil generating a magnetic field induced therein when an action potential fires along an axon along a target nerve;
    an external stimulating device for generating a stimulating signal for stimulation of the target nerve; the external stimulating device comprising:
      a receiving coil for producing a feedback signal based on the generated magnetic field induced in the transmitting coil; and
      a processor for adjusting a stimulating signal parameter of the stimulating signal based on the feedback signal.

11. The system in accordance with claim 10, further comprising signal conditioning and amplification circuitry for reducing noise and amplifying the feedback signal.

12. The system in accordance with claim 10, wherein the stimulating signal parameter is one of amplitude, frequency or a waveform itself.

13. The system in accordance with claim 10, wherein the processor is programmed so that when the feedback signal is zero indicating that the target nerve was not stimulated nor was the action potential fired, the stimulating signal parameter is adjusted; whereas when the feedback signal is greater than zero indicating that the target nerve was stimulated and the action potential was fired, no adjustment is made to the stimulating signal parameter.

14. The system in accordance with claim 10, wherein adjustment of the stimulating signal parameter is in predetermined increments.

15. The system in accordance with claim 14, wherein adjustment of the stimulating signal parameter is in increments of approximately 0.5 V.

16. The system in accordance with claim 13, further comprising an alarm adapted to be activated if the adjusted stimulating signal parameter exceeds a predetermined maximum threshold allowed without detecting the firing of the action potential in the target nerve.

17. The system in accordance with claim 13, wherein the external stimulating device is shut off, if the adjusted stimulating signal parameter exceeds a predetermined maximum threshold allowed without detecting the firing of the action potential in the target nerve.

18. The system in accordance with claim 10, wherein the implantable transmitting coil serves a dual function of monitoring the firing of the action potential along the axon of the target nerve and inducing the feedback signal in the receiving coil of the external stimulating device.

\* \* \* \* \*